· US009555230B2

(12) United States Patent
Jochum et al.

(10) Patent No.: US 9,555,230 B2
(45) Date of Patent: Jan. 31, 2017

(54) PORT FOR A CATHETER (71) Applicant: Fresenius Kabi Deutschland GmbH, Bad Homburg (DE)

(72) Inventors: Christoph Jochum, Nidderau (DE); Martina Papiorek, Hünfelden (DE); Rainer Schumacher, Taunusstein (DE); Hans Haindl, Wenningsen (DE); Markus Kämereit, Nottuln (DE); Klaus Kleve, Warendorf (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 14/787,715

(22) PCT Filed: Feb. 24, 2014

(86) PCT No.: PCT/EP2014/053552
§ 371 (c)(1),
(2) Date: Oct. 28, 2015

(87) PCT Pub. No.: WO2014/177298
PCT Pub. Date: Nov. 6, 2014

(65) Prior Publication Data
US 2016/0106966 A1 Apr. 21, 2016

(30) Foreign Application Priority Data
May 3, 2013 (EP) .................................. 13166447

(51) Int. Cl.
*A61M 39/02* (2006.01)
*A61M 39/10* (2006.01)
(Continued)

(52) U.S. Cl.
CPC ...... *A61M 39/0208* (2013.01); *A61M 39/1011* (2013.01); *A61M 39/04* (2013.01);
(Continued)

(58) Field of Classification Search
CPC ................. A61M 39/0208; A61M 2039/0229; A61M 2039/0235; A61M 39/12; A61M 39/1011
See application file for complete search history.

(56) References Cited

U.S. PATENT DOCUMENTS

| 4,723,948 A | 2/1988 | Clark et al. |
| 5,718,682 A | 2/1998 | Tucker |

(Continued)

FOREIGN PATENT DOCUMENTS

| EP | 1675641 | 3/2008 |
| EP | 2561899 | 2/2013 |

OTHER PUBLICATIONS

Written Opinion of the International Searching Authority, counterpart International Appl. No. PCT/EP2014/053552 (mailed Mar. 27, 2014), with English Translation.

(Continued)

Primary Examiner — Kevin C Sirmons
Assistant Examiner — Shefali Patel
(74) Attorney, Agent, or Firm — Cook Alex Ltd.

(57) ABSTRACT

A port for a catheter includes a housing, a chamber arranged in the housing for receiving a medically active substance, a connecting piece for connecting the catheter to produce a flow connection between the chamber and the catheter, and at least one lever, mounted to be pivotable about a pivot axis and realized to allow the catheter to be fitted onto the connecting piece in a first pivot position and to hold the catheter in a clamping manner on the connecting piece in a second pivot position. The at least one lever has different first and second portions. The first portion carries a latching device for latching the at least one lever with the housing and/or with a first portion of a further lever in the second pivot position. The second portion has a clamping device for (Continued)

holding the catheter in the clamping manner in the second pivot position.

20 Claims, 7 Drawing Sheets

(51) Int. Cl.
 *A61M 39/04* (2006.01)
 *A61M 39/12* (2006.01)
(52) U.S. Cl.
 CPC ..... *A61M 39/12* (2013.01); *A61M 2039/0229* (2013.01); *A61M 2039/0235* (2013.01)

(56) References Cited

U.S. PATENT DOCUMENTS

| | | |
|---|---|---|
| 2007/0123831 A1 | 5/2007 | Haindl et al. |
| 2008/0319421 A1 | 12/2008 | Bizup et al. |
| 2011/0160673 A1 | 6/2011 | Magalich et al. |
| 2012/0109068 A1* | 5/2012 | Vendely ............. A61M 39/1011 604/175 |

OTHER PUBLICATIONS

International Search Report, counterpart International Appl. No. PCT/EP2014/053552 (mailed Mar. 27, 2014) with English Translation, 6 pages.

* cited by examiner

Fig. 6

PORT FOR A CATHETER

The present application is a U.S. National Stage of PCT International Patent Application No. PCT/EP2014/053552, filed Feb. 24, 2014, which claims priority to EP Application No. 13166447.6, filed May 3, 2013, both of which are hereby incorporated herein by reference.

BACKGROUND

The invention relates to a port for a catheter according to the preamble of claim 1.

A port of this type includes a chamber for receiving a medically active substance, a connecting piece for connecting a catheter in order to produce a flow connection between the chamber and the catheter, and at least one lever which is mounted so as to be pivotable about a pivot axis of the housing. The at least one lever is realized to allow the catheter to be fitted onto the connecting piece in a first pivot position and to hold the catheter in a clamping manner on the connecting piece in a second pivot position.

A port of this type, such as is known from EP 1 675 641 B1, can be implanted in a patient by being inserted, for example, under the skin of a patient (subcutaneously) and fastened there. The port then serves for infusing medical drugs, blood products, nutrients and other medically active substances into the venous or arterial system of a patient. By means of the port, an active substance can be administered to a patient in particular in a repeated manner over a fairly long period. Because the port, in this case, is able to be fully implanted under the skin of a patient, the risk of infection is reduced, and active substances can be administered over a fairly long period in a targeted manner for treating a patient without the patient having to be received in a stationary manner into a hospital for this purpose and without the port obstructing the patient considerably in his everyday life.

In the case of an infusion, an active substance is diverted from the chamber contained in the housing via a catheter which is connected to the connecting piece of the port and is supplied to the patient, for example to the venous or arterial system of the patient. The catheter, in this connection, is implanted together with the port in the patient and is placed in such a manner that the active substance is transported to a predetermined site in the patient.

In the case of such a port, care must be taken to ensure that the catheter which is fitted onto the connecting piece cannot slip from the connecting piece when the port is implanted and consequently become detached from the port. To this end, the port described in EP 1 675 641 B1 comprises clamping jaws which stand away from the housing of the port in a first position and, for holding the catheter in a clamping manner on the housing, can be transferred into a second position in which they receive the catheter between them in a clamping manner.

U.S. Pat. No. 4,723,948 discloses a port where a catheter can be connected to a connecting piece of the port by means of a sleeve. The sleeve consists of two parts which are connected together by means of a film hinge and, for connecting the catheter to the connecting piece in a positive locking manner, enclose the connecting piece in a closed position of the sleeve.

There is a need for a port which makes it easy to fit a catheter onto a connecting piece and which can provide a reliable hold between the catheter and the connecting piece in a simple and easy to handle manner. In this case, it must be taken into consideration that the handling of such a port can frequently be made more difficult as a result of a user, for example a doctor during an operation, often wearing gloves such that the handling should be correspondingly simple and possible without any great expenditure of effort.

SUMMARY

It is the object of the present invention to provide a port for a catheter which enables a catheter to be held in a reliable manner on the port and is simple to handle.

Said object is achieved by an article with the features of claim 1.

It is accordingly provided that the at least one lever comprises a first lever portion and a second lever portion which is different to the first lever portion. The first lever portion carries a latching device for latching the at least one lever with the housing and/or with a first lever portion of a further lever in the second pivot position and the second lever portion carries a clamping device for holding the catheter in a clamping manner in the second pivot position.

The present invention proceeds from the concept of providing one or several levers, which in each case comprise two lever portions, for fixing the catheter on the connection piece. A first lever portion, in this connection, carries a latching device, whilst a second lever portion comprises a clamping device. The latching device serves for the purpose of latching the lever in its second position, in which it is realized to hold a catheter in a clamping manner on the connecting piece, with the housing of the port and/or of fixing it on the housing by latching with a first lever portion of a further lever such that the lever cannot easily be pivoted out of its second position, at least not without releasing the latching. The clamping hold of the catheter on the connecting piece is provided, in this connection, by means of the clamping device which acts in a clamping manner on the catheter and in the second position consequently holds the catheter securely and reliably on the port.

In the first position of the at least one lever, the catheter can be fitted onto the port such that the catheter can consequently be connected to the port, for example, prior to the implanting of the port. In said first position, a clamping portion of the clamping device is removed from the connecting piece in such a manner that the catheter is able to be fitted onto the connecting piece, for example pushed onto the connecting piece, without this being obstructed by the clamping portion of the second lever portion. When being transferred into the second pivot position, the clamping portion is then moved closer to the catheter as a result of pivoting the lever such that the catheter is clamped between the clamping portion and the connecting piece and, as a result, is locked on the port.

The second lever portion is preferably shorter than the first lever portion. For example in the first position of the lever, the first lever portion can stand away from the housing and can be manually actuated to transfer the lever into its second position by being pivoted toward the housing. As a result of the first lever portion being longer than the second lever portion, an advantageous lever ratio is produced which enables the lever to pivot with a comparatively small amount of actuating force, at the same time, however, it provides a comparatively large amount of clamping force on the second lever portion for holding the catheter in a clamping manner on the connecting piece.

In principle, the first lever portion and the second lever portion can be a component part of the same lever arm, the second lever portion, however, being different in lever length, preferably shorter than the first lever portion. The first lever portion and the second lever portion, however, preferably extend in different directions from the pivot axis by the first lever portion extending, for example, in a first direction from the pivot axis and the second lever portion extending in a second direction from the pivot axis which is opposite to the first direction.

In an advantageous manner, at least one clamping rib, which extends transversely, for example perpendicularly, with respect to a pivoting direction, along which the at least one lever is pivotable for transferring from its first position into its second position, is arranged on the clamping portion of the second lever portion. As a result of such transversely extending clamping ribs, which are moved closer to the catheter fitted on the connecting piece when the lever is transferred into its second position, the catheter is clamped in a particularly secure manner on the connecting piece, ensuring the catheter is held in a reliable manner on the port.

The latching device which is realized on the first lever portion can comprise, for example, a latching hook which engages in a latching manner with an associated latching projection of the housing and/or of a further lever in the second pivot position, that is to say with the catheter locked on the port. As a result of the latching device being arranged on the preferably longer first lever portion of the lever, a comparatively small latching force can suffice for locking the lever securely in its second position. As a result additionally of the latching device being spatially separated from the clamping device, it can be ensured that when the lever is transferred into its second position, the latching device snaps-in in an audible manner such that a user receives feedback regarding the achieving of the second pivot position of the lever and consequently the achieving of the clamping position. As a result of the latching device being spatially separated from the clamping device and consequently from the catheter, noise generation during the latching-in process cannot be damped such that a user experiences feedback that is haptically and/or acoustically perceivable and preferably also pleasant.

In principle, the latching serves for the purpose of holding the at least one lever securely in its second pivot position in order, in particular in the case of an implanted port, to avoid the lever pivoting out—which would be accompanied by release of the locking of the catheter on the port. In this case, it can be provided that the latching of the at least one lever with the housing or with another lever is developed so as to be releasable by providing on a housing bottom of the housing an actuating opening, through which access can be gained to the latching device, for example by means of a suitable shaped piece, in order to release the latching hooks of the latching device from their positive locking connection with the latching projections of the housing and/or of the further lever.

In an advantageous development, the port comprises two levers which comprise in each case a first lever portion and a second lever portion which is different to the first lever portion. The levers are pivotable in this connection preferably about pivot axes which are aligned substantially in the same manner and extend in particular parallel to one another, the pivot axes extending preferably almost approximately transversely, in particular perpendicularly, to a direction of extension of the connecting piece which is realized as a cannula. As a result of pivoting the levers into their second pivot position in each case, it is consequently possible to clamp a catheter fitted onto the connecting piece on both sides between the levers and the connecting piece such that a particularly secure hold of the catheter on the port is ensured.

The catheter is locked on the port in the second pivot position. If the levers, in contrast, take up the first pivot position, the clamping portions on the second lever portions of the levers are removed from the connecting piece such that the catheter is able to be pushed onto the connecting piece. In this connection, the levers preferably form a through-opening between their second lever portions by comprising suitable recesses through which the catheter can be guided in the first pivot position of the levers to be fitted onto the connecting piece.

The levers do not necessarily have to be latched with the housing. It is also conceivable and possible to develop the latching devices of the two levers such that the two levers are able to latch together and thus hold each other in the second pivoted-in position.

In order to transfer the levers from their first position into the second position for locking a catheter fitted onto the connecting piece, the levers have to be pivoted. In order to ensure in this case that the pivoting movement of the levers is effected in a uniform manner, the levers can comprise in each case a toothing on their second lever portion, the toothings of the levers engaging together in such a manner that when the one lever is pivoted, the other lever is also pivoted in a synchronous manner at the same time. The levers are consequently only able to be pivoted in a synchronous manner such that the clamping portions of the clamping device of the two levers are moved closer to the catheter in a uniform manner and the clamping of the catheter between the levers and the connecting piece is consequently produced in a synchronous manner.

When transferring the at least one lever into its second position, the lever is preferably moved closer to the housing. At least one pressure point, which is in the form of a bulge and is to be moved into engagement with an indentation on the at least one lever when transferring the at least one lever from the first pivot position into the second pivot position, is arranged on the housing, a certain predetermined expenditure of force being necessary to move the pressure point on the housing into engagement with the indentation on the lever. In this way it can be ensured that a pivoting of the at least one lever into its second pivot position is only able to be effected in a conscious manner, by a user, when pivoting the lever into its second pivot position, experiencing a resistance on account of the pressure point which he has to overcome in order to move the lever into the second pivot position.

In an alternative embodiment, the lever is not provided with an indentation. The pressure point is overcome when a certain, predefined expenditure of force is provided without any "meshing" taking place.

For example, an inspection opening, through which it is possible to inspect visually whether a catheter is fitted onto the connecting piece and is held on the connecting piece in a correct manner, can be provided additionally on a base plate of the housing. The inspection opening allows the connecting piece to be seen such that it is possible to check, even when the clamping connection has been produced, whether the catheter is connected to the port in the desired manner.

The port preferably comprises a membrane which is held on the housing and is able to be pierced by means of a puncturing cannula in order to inject an active substance into the chamber of the housing. In order, in this connection, to prevent a puncturing cannula, when attempting to puncture the membrane, from being able to slide away from the housing and toward the catheter connected to the port—which could potentially result in damage to the catheter—, the housing comprises a deflecting element (also designated as a "baffle edge") which is realized on a side of the membrane which points toward the connecting piece and prevents a puncturing cannula from slipping toward the catheter connected to the connecting piece of the port. The deflecting element can be, for example, a component part of a groove-shaped indentation which extends on the housing and guides the puncturing cannula away from the catheter if the puncturing cannula should slip.

BRIEF DESCRIPTION OF THE FIGURES

The concept underlying the invention is to be explained in more detail below by way of the exemplary embodiments shown in the figures, in which.

DETAILED DESCRIPTION

FIGS. 1 to 7A, 7B show an exemplary embodiment of a port 1 to which a catheter 2 is able to be connected.

Figure 1:
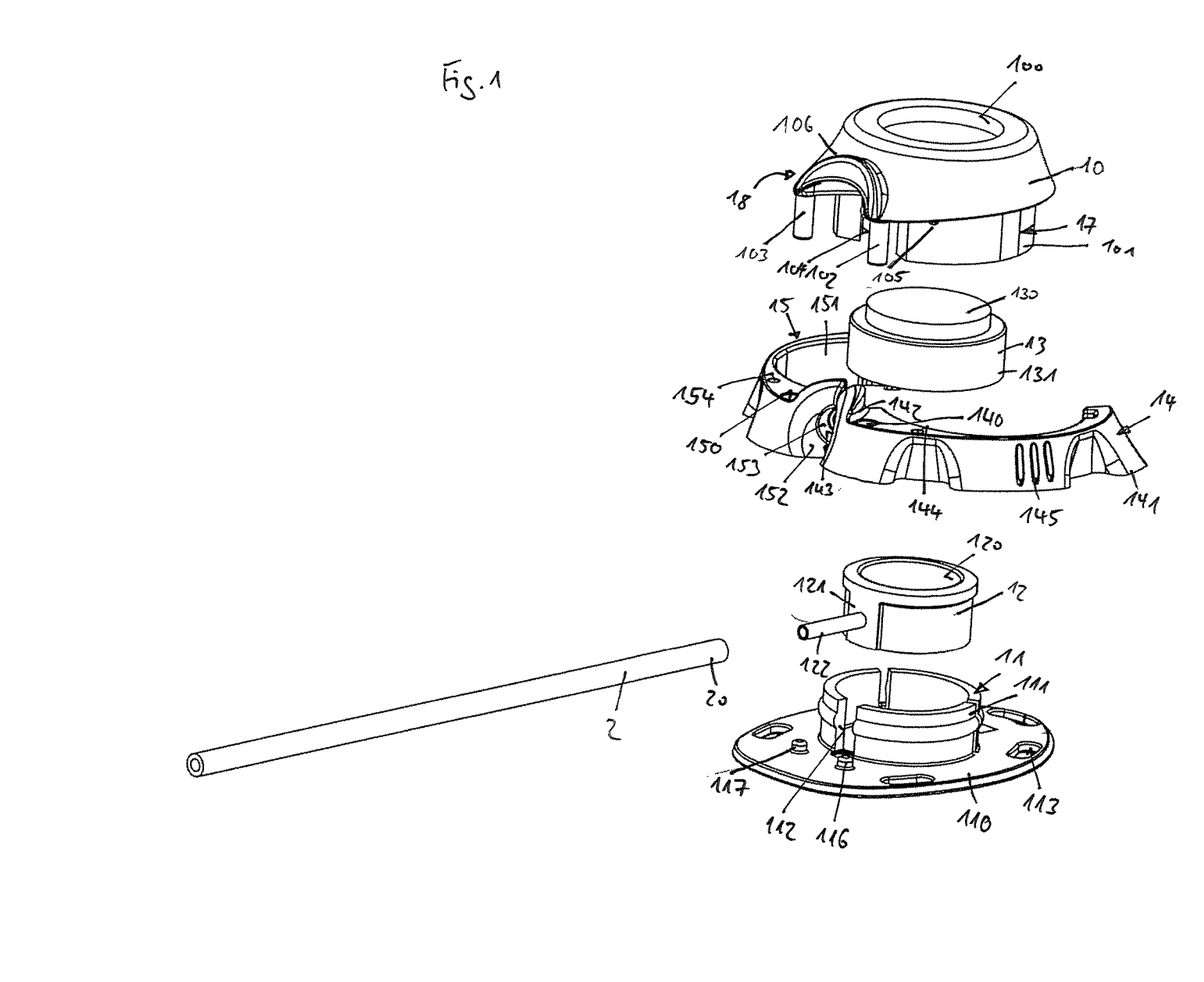
FIG. 1 shows an exploded view in perspective of a port with a catheter to be connected thereto.
Figure 2:
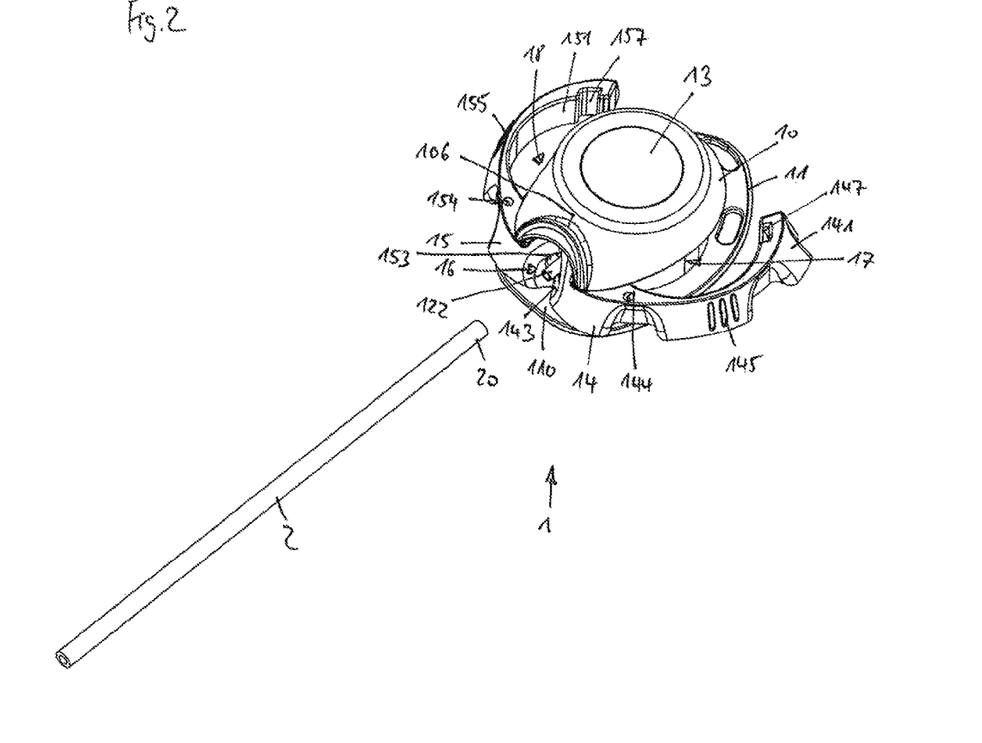
FIG. 2 shows a perspective view of the port with the catheter to be connected thereto, prior to the connecting of the catheter.

The port 1 comprises a housing which is formed by housing parts 10, 11 and surrounds a chamber 120 which is formed in an insert 12.

The port 1 together with a catheter 2 connected thereto can be implanted into a patient. An active substance situated in the chamber 120 can then be passed to an active site in the patient by means of the catheter 2 in order to supply an active substance, for example a medical drug, nutrients or other medical liquids to the patient in this manner.

The port 1 comprises a membrane 13 which, in the assembled state of the port 1, is inserted by way of a head portion 130 into an opening 100 of the upper housing part 10 and closes off the chamber 120 of the insert 12 toward the top. The membrane 13 can be punctured by a puncturing cannula in order to inject an active substance into the chamber 120 in this way and consequently fill the port 1.

The lower housing part 11 comprises a base plate 110 with seam holes 113 for fastening the port 1 in a patient and a plug-in portion 111 which is to be plugged into a containing means 101 of the upper housing part 10. To assemble the port 1, the insert 12 is inserted into the plug-in portion 111 in such a manner that a projection 121 of the insert 12 moves into engagement with a recess 112 of the plug-in portion 111 of the lower housing part 11 and the insert is consequently held non-rotatably on the lower housing part 11. A connecting piece 122, which is in the form of a cannula and, in the assembled state of the port, extends through the recess 112 of the lower housing part 11 and creates a connection for the catheter 2 by means of which a flow connections between the catheter 2 and the chamber 120 is able to be produced, is arranged in the region of the projection 121. Consequently, a fluid is able to flow out of the chamber 120 into the catheter 2 by means of the connecting piece 122 when the catheter 2 has been connected to the connecting piece 122.

Figure 4A:
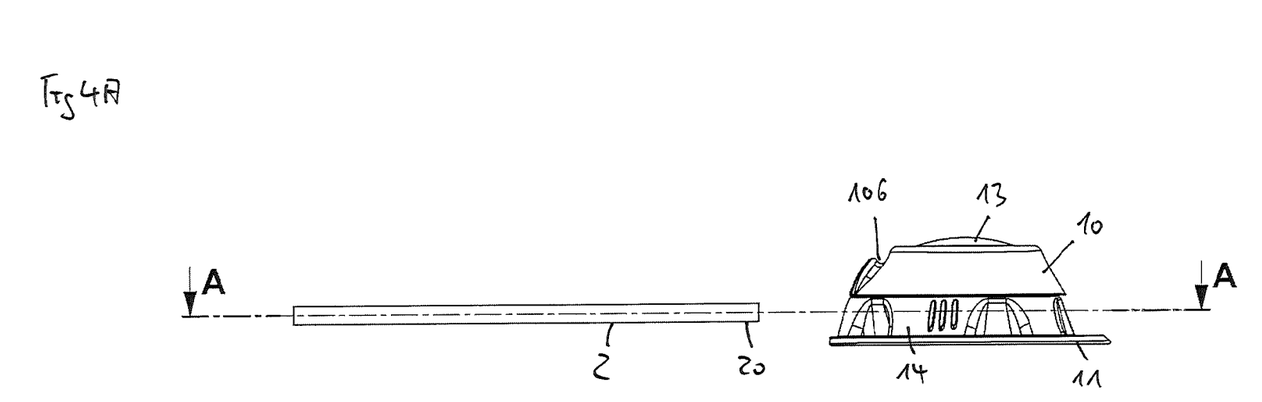
FIG. 4A shows a side view of the port with the catheter to be connected thereto, prior to the connecting of the catheter.
Figure 4B:
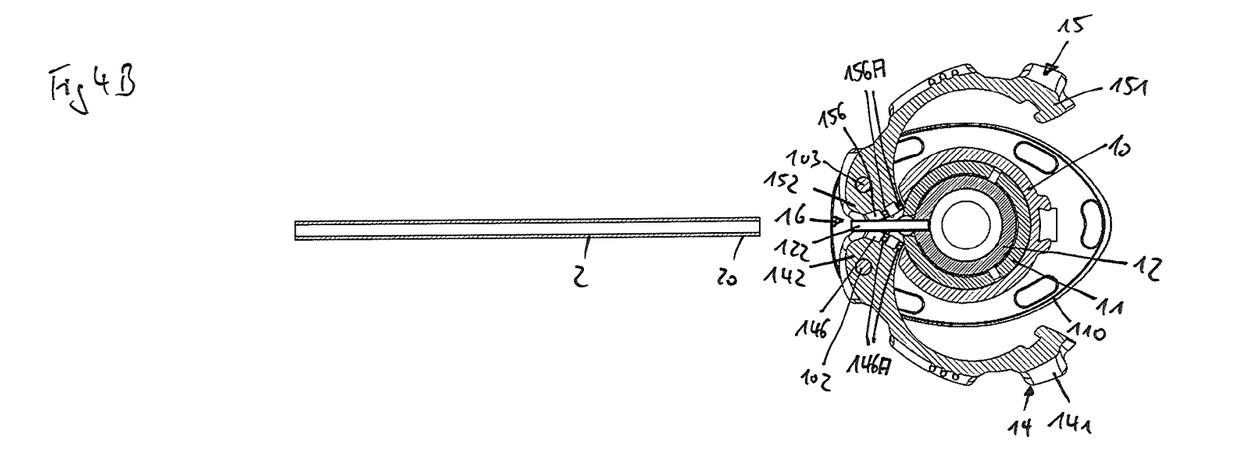
FIG. 4B shows a sectional view along the line A-A according to FIG. 4A.

In the assembled state of the port 1, the plug-in portion 111 of the lower housing part 11 is plugged into the containing means 101 of the upper housing part 10, as can be seen, for example, from FIG. 4B. The connecting part 122 in the form of the cannula extends, in this case, through a recess 104 on the containing means 101 of the upper housing part 10 and consequently protrudes outwardly beyond the containing means 101. In this connection, a bottom portion 131 of the membrane 13 lies between the insert 12 and an upper edging of the opening 100 of the upper housing part 10 such that the membrane 13 is held in a clamping manner between the insert 12 and the edging of the opening 100.

The port 1 comprises two levers 14, 15 which are mounted so as to be pivotable about pivot axes 102, 103 on the upper housing part 10 and serve for the purpose of locking the catheter 2 when it is fitted onto the connecting piece 122, so that, with the port 1 implanted, the catheter 2 is not able to become detached from the connecting piece 122. The levers 14, 15 make it possible, in this connection, in a pivoted-out first position (see FIG. 2) for the catheter 2 to be fitted onto the connecting piece 122 and hold the catheter 2 in a pivoted-in second position (see FIG. 3) in a clamping manner on the connecting piece 122.

The levers 14, 15 comprise in each case two lever portions 141, 142 or 151, 152. A latching device in the form of latching hooks 147, 157 (see FIG. 5B) which, in the pivoted-in second position of the levers 14, 15, engage with latching projections 107, 108 on the upper housing part 10 and consequently latch the levers 14, 15 with the upper housing part 10, are arranged on the longer first lever portion 141, 151. A clamping device in the form of a clamping portion 146, 156, which has clamping ribs 146A, 156A (see FIG. 5B) and serves in the pivoted-in second position of the levers 14, 15 for the purpose of clamping the catheter 2 with the connecting piece 122 such that the catheter 2 is not able to slip from the connecting piece 122 in an unintentional manner, is arranged in contrast on the shorter second lever portion 142, 152.

As a result of the first lever portion 141, 151 being realized in a clearly longer manner than the second lever portion 142, 152 with the clamping device arranged thereon and the levers 14, 15 being actuated by means of the first lever portion 141, 151 with the gripping ribs 145, 155 arranged thereon (see FIG. 2), the levers 14, 15 can be manually pivoted in an easy manner in an associated pivoting direction S1, S2 for locking the catheter 2 on the port 1, on account of the lever ratios a comparatively large amount of clamping force being produced on the second lever portion 142, 152 with a comparatively small amount of actuating force for clamping the catheter 2 with the second lever portion 122. The levers 14, 15 are actuated in a simple, haptically pleasant manner for transferring the levers 14, 15 from the pivoted-out first position (see FIG. 2) into the pivoted-in second position (see FIG. 3), which is also easily able to be carried out by a user wearing operating gloves.

In addition, as a result of the latching device in the form of the latching hooks 147, 157 being arranged on the end of the first lever portion 141, 151 remote from the pivot axis 102, 103, the latching device only has to apply a comparatively small latching force in order to hold the levers 14, 15 reliably in their pivoted-in second position. Over and above this, when the levers 14, 15 are transferred from the pivoted-out first position into the pivoted-in second position, the snapping of the latching hooks 147, 157 into positive locking engagement with the latching projections 107, 108 is not damped such that, on the one hand, the latching process snaps securely in and, on the other hand, a clearly audible snapping-in noise is generated, which supplies the user with feedback concerning the latching produced.

The levers 14, 15 comprise on each of their second lever portions 142, 152 a recess 143, 153 in the form of an indentation and said recesses together provide a through-opening 16 for the fitting of the catheter 2 onto the connecting piece 122 in the pivoted-out first position of the levers 14, 15. In the pivoted-out first position (see FIG. 2 and FIGS. 4A and 4B), the catheter 2 can consequently be inserted by way of an end 20 into the through-opening 16 and can be pushed onto the connecting piece 122 until the end 20 of the catheter 2 abuts against the insert 12, as is shown in FIG. 5B.

Figure 3:
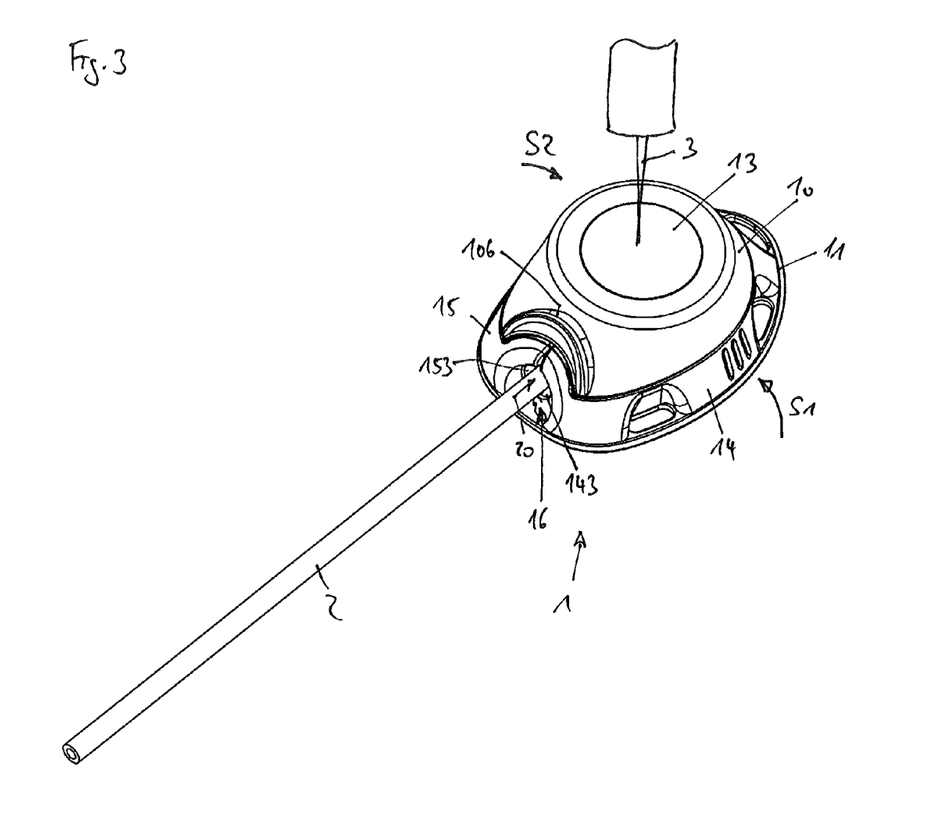
FIG. 3 shows a perspective view of the port with the catheter connected thereto.
Figure 5A:
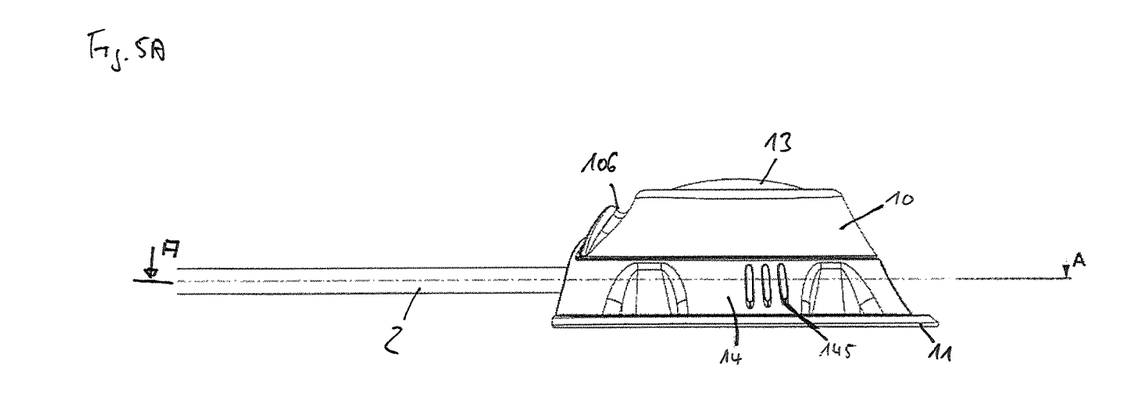
FIG. 5A shows a side view of the port with the catheter connected thereto.
Figure 5B:
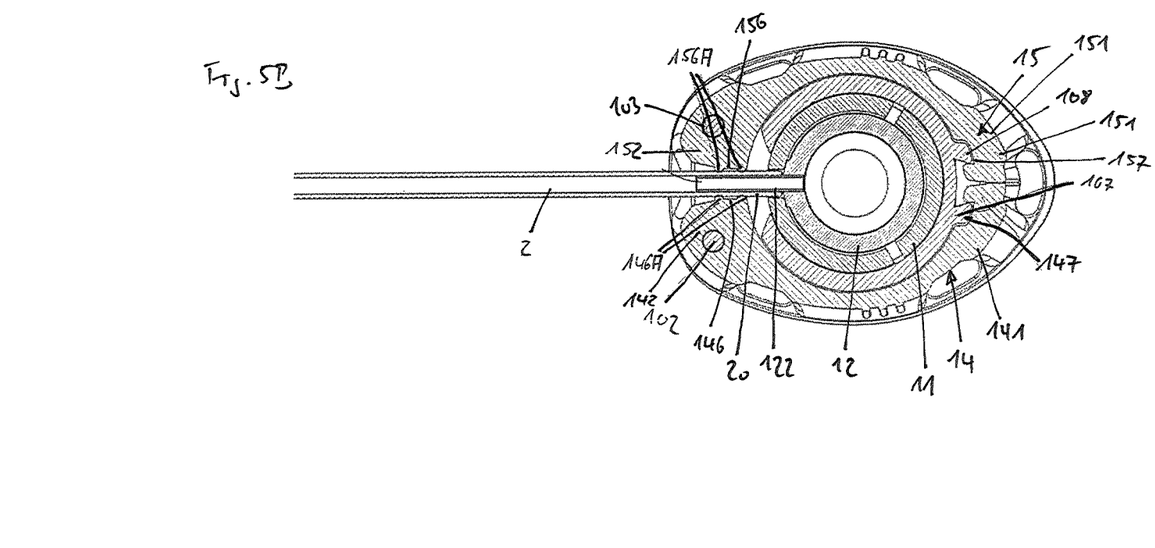
FIG. 5B shows a sectional view along the line A-A according to FIG. 5A.

To lock the catheter 2 on the connecting piece 122, the levers 14, 15 are then pivoted into receiving slots 17, 18 which are formed between the base plate 110 of the lower housing part 11 and the upper housing part 10, such that the levers 14, 15 pass into their pivoted-in second position and the latching hooks 147, 157 snap into engagement with the latching projections 107, 108 on the upper housing part 10 (see FIG. 3 and FIGS. 5A and 5B).

As a result, the clamping portions 146, 156 with the clamping ribs 146A, 156A arranged thereon on the second lever portions 142, 152 of the levers 14, 15 are moved closer to the catheter 2 arranged on the connecting piece 122 and are moved into clamping abutment with the end 20 of the catheter 2 such that the catheter 2 is locked on the connecting piece 122 (see FIG. 5B). The catheter 2 is consequently held fixedly on the connecting piece 122 and cannot easily slip from the connecting piece 122, at least not in an unintentional manner.

In order to prevent the levers 14, 15 being pivoted in an unintentional manner even prior to fitting the catheter 2 onto the connecting piece 122, an indentation 144, 154, which is to be moved into engagement with a pressure point 105, 106 on the upper housing part 10, is arranged on each lever 14, 15. When the levers 14, 15 are pivoted-in, said pressure point 105, 106 has to be overcome, which requires a certain force to be applied and consequently counteracts an inadvertent, involuntary pivoting-in of the levers 14, 15.

Offset axially along the pivot axis 102, 103 with respect to the clamping portion 146, 156, each lever 14, 15 comprises a toothing 149, 159 and the toothings mesh together and cause the levers 14, 15 only to be able to be pivoted synchronously with one another. It is consequently not possible to pivot the one lever 14, 15 without the other lever 15, 14, which causes the clamping portions 146, 156 to be moved in a synchronous manner into clamping abutment with the catheter 2 when the levers 14, 15 are pivoted-in. This is shown in FIG. 7B.

Figures 7A, 7B:
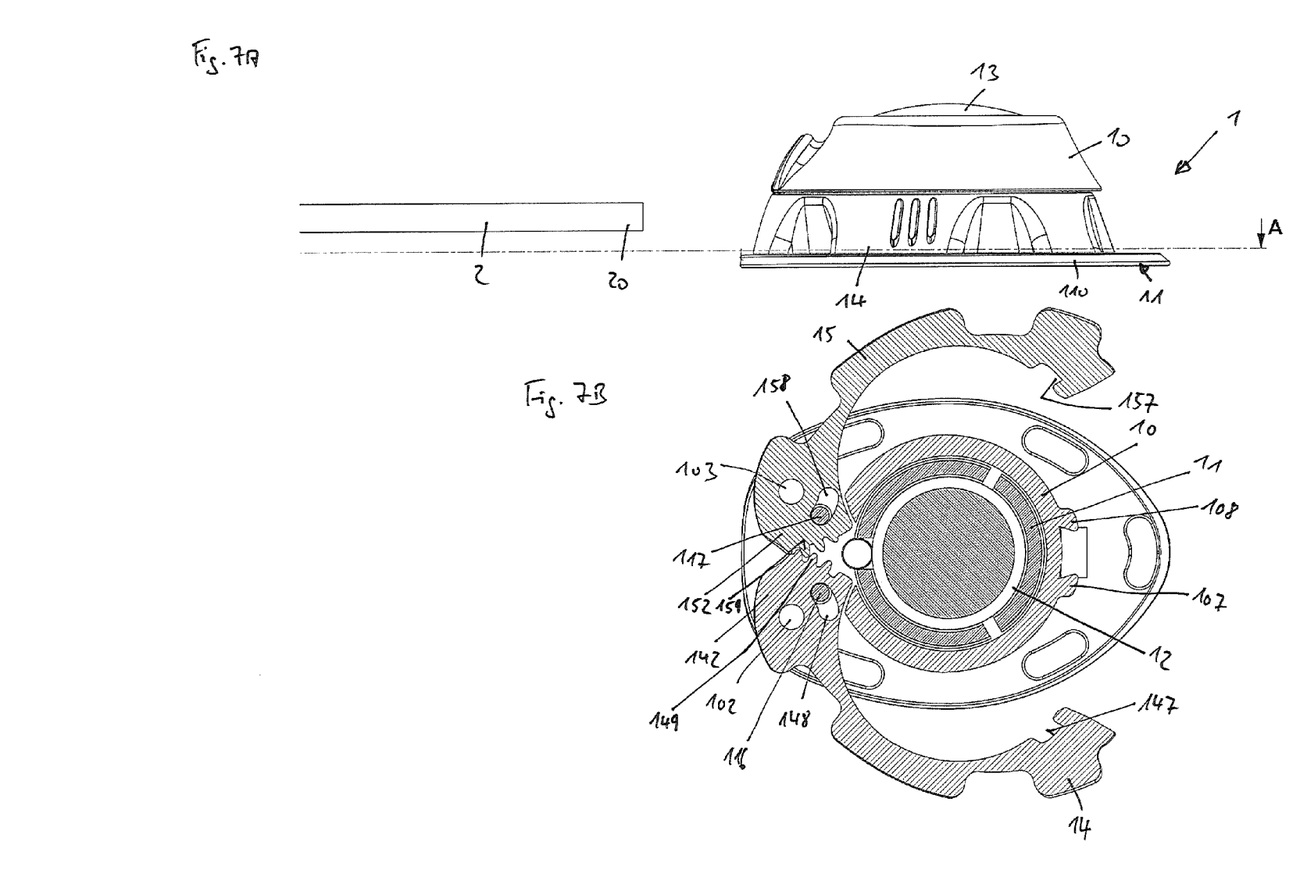
FIG. 7A shows a side view of the port with the catheter to be connected thereto, prior to the connecting of the catheter.
FIG. 7B shows a sectional view along the line A-A according to FIG. 7A.

As can also be seen from FIG. 7B, the levers 14, 15 comprise in the region of the second lever portion 142, 152 in each case an elongated hole 148, 158 in which a guide pin 116, 117 engages, on the base plate 110 of the lower housing part 11. On the one hand, the pivoting movement of the levers 14, 15 is guided by means of the guide pins 116, 117 which engage in the elongated holes 148, 158. On the other hand, an end position of the levers 14, 15, in particular in the pivoted-out first position, is defined such that the levers 14, 15 are not able to be pivoted-out beyond the position shown in FIG. 7B.

Figure 6:
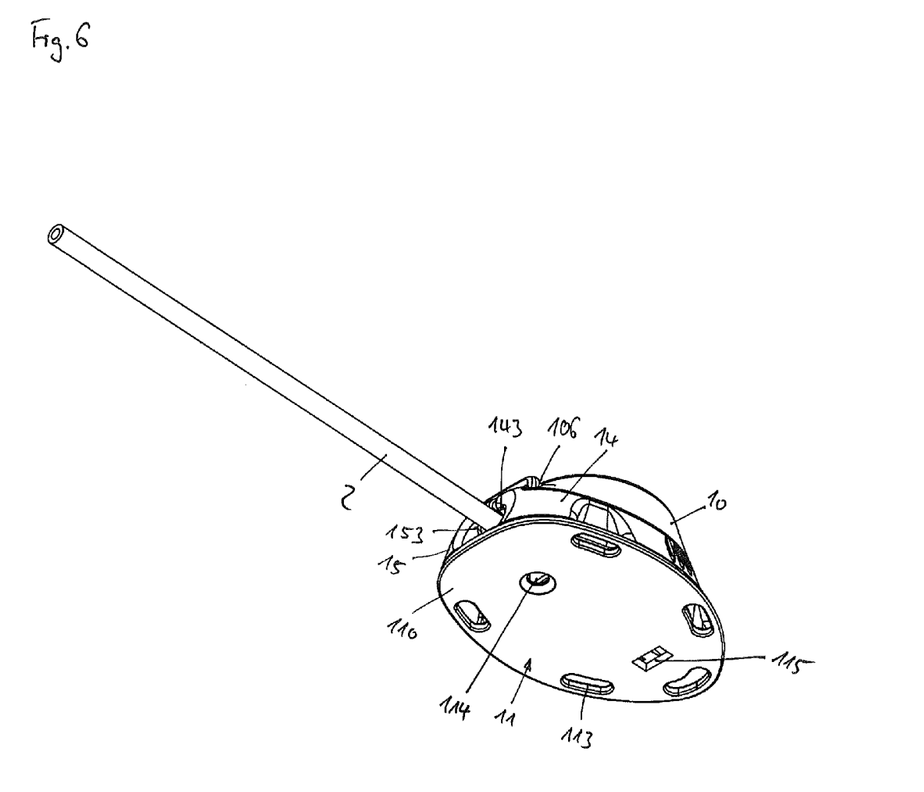
FIG. 6 shows a perspective view of the port with the catheter connected thereto, obliquely from below.

As can be seen from the view obliquely from below according to FIG. 6, on the one hand an inspection opening 114 and on the other hand an actuating opening 115 are arranged on the base plate 110 of the lower housing part 11. By means of the inspection opening 114, it is possible to check visually whether the catheter 2 is fitted correctly onto the connecting piece 122 by way of its end 20. If it can be verified visually that the catheter 2, for example, has been pushed far enough onto the connecting piece 112, the levers 14, 15 can be pivoted-in to lock the catheter 2 on the port 1. The actuating opening 115 serves for the purpose of releasing again, where applicable, the latching of the levers 14, 15 with the upper housing part 10 in the pivoted-in second position in order to be able to remove the catheter 2 from the port 1. To this end, a tool in the form of a shaped part can be inserted through the actuating opening 115 in order to eliminate the positive locking connection between the latching hooks 147, 157 and the associated latching projections 107, 108 and to release the latching in this way.

To fill the chamber 120 of the insert 12, the membrane 13 is pierced by means of a puncturing cannula 3 (see FIG. 3), and an active substance is injected into the chamber 120. This is effected, as a rule, with a port 1 that has been implanted into a patient such that the membrane 3 is not freely visible to the user operating the puncturing cannula 3, for example a nursing sister, and the port 1 with its membrane 13 has to be felt. In order, in this connection, to reduce the risk during the attempt of piercing the membrane 13 with the puncturing cannula 3, the puncturing cannula 3 sliding off the upper housing part 10 and puncturing the catheter 2, a deflecting element 106, which is integrally formed on the upper housing part 10 in the manner of a groove, extends transversely with respect to an (imaginary) connecting line between the membrane 13 and the catheter 2 and guides the puncturing cannula 31 away from the catheter 2 if it should slip in the direction of the catheter 2, is provided on the upper housing part 10 on a side of the membrane 13 facing the catheter 2. The catheter 2 is consequently shielded.

The housing parts 10, 11 of the port 1 can be produced in an advantageous manner from a biocompatible material, for example a biocompatible plastics material. The insert 12, in contrast, can consist of a material that is resistant to the active substance, for example a metal material or a ceramic material. Such a material is resistant to the most varied active substances and also comprises sufficient strength such that the insert 12 is not able to be pierced by a puncturing cannula 3.

The concept underlying the invention is not limited to the exemplary embodiments depicted previously, but can also be realized in a completely different manner.

In particular, it is not absolutely necessary for the port to comprise the described three-part design with an upper housing part, a lower housing part and an insert that is contained thereby. In principle, other designs which do not use a separate insert, for example, are also conceivable and possible.

In an alternative embodiment (not shown), the levers 14, 15 do not latch with the housing part 10 but with themselves, for example as a result of a latching projection being realized on the one hook and a latching hook being realized on the other lever. The fixing with the housing, in particular with the housing part 10, 11, can be achieved in this case, for example, by means of a positive locking connection and/or a frictional locking connection. It is also possible for a further latching device to be provided on at least one lever 14, 15 and on the housing part 10, 11 such that along with a latching of the two levers 14, 15, there is also a latching with the housing part 10, 11. The advantages named with reference to the latching of the levers 14, 15 with the housing part 10 are naturally also provided in the case of said embodiment.

In a further alternative embodiment (not shown), the lever 14, 15 does not include any indentation 144, 145, the pressure point 105 is simply overcome without the pressure point 105 engaging in an indentation of the lever 14, 15.

LIST OF REFERENCES

- 1 Port
- 10 Housing part
- 100 Opening
- 101 Containing means
- 102, 103 Pivot axis
- 104 Recess
- 105 Pressure point
- 106 Deflecting element (baffle edge)
- 11 Housing part
- 110 Base plate
- 111 Plug-in portion
- 112 Recess
- 113 Seam holes
- 114 Inspection opening
- 115 Actuating opening
- 116, 117 Guide pin
- 12 Insert
- 120 Chamber
- 121 Projection
- 122 Connecting piece (cannula)
- 13 Membrane
- 130 Head portion
- 131 Lower portion
- 14, 15 Lever
- 140, 150 Bearing opening
- 141, 151 Lever portion
- 142, 152 Lever portion
- 143, 153 Recess
- 144, 154 Indentation
- 145, 155 Gripping ribs
- 146, 156 Clamping portion
- 146A, 156A Clamping ribs
- 147, 157 Latching hook
- 148, 158 Elongated hole
- 149, 159 Toothing
- 16 Through-opening
- 2 Catheter
- 20 End
- 3 Puncturing cannula

The invention claimed is:

1. A port for a catheter, the port comprising:
a housing,
a chamber arranged in the housing for receiving a medically active substance,
a connecting piece for connecting the catheter in order to produce a flow connection between the chamber and the catheter, and
at least one lever which is mounted so as to be pivotable about a pivot axis, wherein the at least one lever is realized to allow the catheter to be fitted onto the connecting piece in a first pivot position and to hold the catheter in a clamping manner on the connecting piece in a second pivot position,
the at least one lever comprising a first lever portion and a second lever portion, which is different to the first lever portion and is disposed on an opposite side of the pivot axis from the first lever portion, wherein the first lever portion carries a latching device for latching the at least one lever with the housing and/or with a first lever portion of a further lever in the second pivot position and the second lever portion carries a clamping device for holding the catheter in the clamping manner in the second pivot position.

2. The port as claimed in claim 1, wherein the clamping device includes a clamping portion which is removed from the connecting piece in the first pivot position in such a manner that the catheter is fittable onto the connecting piece, and in the second pivot position is moved closer to the connecting piece, in comparison to the first pivot position, for holding the catheter in the clamping manner on the connecting piece.

3. The port as claimed in claim 1, wherein the second lever portion is shorter than the first lever portion of the at least one lever.

4. The port as claimed in claim 1, wherein the first lever portion of the at least one lever and the second lever portion extend in different directions from the pivot axis.

5. The port as claimed in claim 1, further comprising at least one clamping rib, which extends transversely with respect to a pivoting direction, along which the at least one lever is pivotable, and is arranged on the second lever portion.

6. The port as claimed in claim 1, wherein the latching device is realized by a latching hook which engages in a latching manner with an associated latching projection of the housing and/or of the further lever in the second pivot position.

7. The port as claimed in claim 1, wherein the latching of the at least one lever with the housing and/or with the further lever is releasable in the second pivot position.

8. The port as claimed in claim 7, wherein for releasing the latching, the housing comprises an actuating opening through which the latching device is actuatable for release.

9. The port as claimed in claim 1, the at least one lever comprising two levers which comprise in each case a first lever portion and a second lever portion which is different to the first lever portion.

10. The port as claimed in claim 9, wherein the levers are pivotable about pivot axes which are aligned in a same manner.

11. The port as claimed in claim 9, wherein a through-opening, through which the catheter is guidable, is realized by the levers between their second lever portions in the first pivot position.

12. The port as claimed in claim 9, wherein the levers comprise in each case a toothing on the second lever portion and the toothings of the levers engage together in such a manner that when one lever of the levers is pivoted, the other lever of the levers is also pivoted.

13. The port as claimed in claim 1, further comprising at least one pressure point, which has to be overcome when transferring the at least one lever from the first pivot position into the second pivot position, and/or has to be moved into engagement with an indentation on the at least one lever, and is arranged on the housing.

14. The port as claimed in claim 1, wherein the housing comprises an inspection opening through which an arrangement of the catheter on the connecting piece in the second pivot position is checkable.

15. The port as claimed in claim 1, further comprising a membrane which is held on the housing and a deflecting element, wherein the deflecting element is arranged and realized on the housing on a side of the membrane which points toward the connecting piece in order to prevent a puncturing cannula from slipping toward the catheter which is connected to the connecting piece of the port.

16. A system comprising:
the port as claimed in claim 1, and
a catheter which is held in the clamping manner on the connecting piece of the port in the second pivot position of the at least one lever and is fittable onto the connecting piece in the first pivot position of the at least one lever.

17. A port for a catheter, the port comprising:
a housing having a front and a rear,
a chamber arranged in the housing for receiving a medically active substance,
a connecting piece for connecting the catheter in order to produce a flow connection between the chamber and the catheter, the connecting piece disposed at the front of the housing, and
at least one lever which is mounted so as to be pivotable about a pivot axis, wherein the at least one lever is realized to allow the catheter to be fitted onto the connecting piece in a first pivot position and to hold the catheter in a clamping manner on the connecting piece in a second pivot position,
the at least one lever comprising a first lever portion and a second lever portion which is different to the first lever portion, wherein the first lever portion carries a latching device for latching the at least one lever with the rear of the housing and/or with a first lever portion of a further lever at the rear of the housing in the second pivot position and the second lever portion carries a clamping device for holding the catheter in the clamping manner in the second pivot position.

18. The port as claimed in claim 17, wherein the second lever portion is disposed on an opposite side of the pivot axis from the first lever portion of the at least one lever.

19. The port as claimed in claim 18, wherein the first lever portion of the at least one lever and the second lever portion extend in opposite directions from the pivot axis.

20. The port as claimed in claim 17, wherein the pivot axis is disposed at the front of the housing.

* * * * *